United States Patent
Simonetti et al.

(10) Patent No.: US 9,803,976 B2
(45) Date of Patent: Oct. 31, 2017

(54) METHODS AND APPARATUS FOR MEASUREMENT OR MONITORING OF WALL THICKNESSES IN THE WALLS OF PIPES OR SIMILAR STRUCTURES

(71) Applicants: Francesco Simonetti, Cincinnati, OH (US); Geir Instanes, Nesttun (NO)

(72) Inventors: Francesco Simonetti, Cincinnati, OH (US); Geir Instanes, Nesttun (NO)

(73) Assignee: Clamp On AS, Bergen (NO)

(*) Notice: Subject to any disclaimer, the term of this patent is extended or adjusted under 35 U.S.C. 154(b) by 226 days.

(21) Appl. No.: 14/692,929

(22) Filed: Apr. 22, 2015

(65) Prior Publication Data

US 2015/0233710 A1    Aug. 20, 2015

(51) Int. Cl.
*G01N 29/04* (2006.01)
*G01B 17/02* (2006.01)

(52) U.S. Cl.
CPC ........... *G01B 17/02* (2013.01); *G01N 29/041* (2013.01)

(58) Field of Classification Search
CPC .............................. G01N 29/041; G01B 17/02
USPC .......................................................... 73/598
See application file for complete search history.

(56) References Cited

U.S. PATENT DOCUMENTS

2013/0263667 A1   10/2013   Volker et al.
2014/0208852 A1    7/2014   Instanes

FOREIGN PATENT DOCUMENTS

| EP | 2 439 527 | 11/2012 |
|---|---|---|
| GB | 2508515 | 6/2014 |
| WO | WO 2004/099764 | 11/2004 |
| WO | WO 2007/139389 | 12/2007 |
| WO | WO 2014/120917 A1 | 8/2014 |

OTHER PUBLICATIONS

Brath, Alex J., et al. "Acoustic formulation of elastic guided wave propagation and scattering in curved tubular structures." Ultrasonics, Ferroelectrics, and Frequency Control, IEEE Transactions on 61.5 (2014): 815-829.

(Continued)

*Primary Examiner* — John Chapman, Jr.
(74) *Attorney, Agent, or Firm* — Francis C. Hand; Carella, Byrne Et Al

(57) ABSTRACT

A method and an apparatus for guided-wave tomographic measurement or monitoring of wall thicknesses of the walls of pipes and similar structures are disclosed. The method is characterized in that use is made of transducers (205) preferably positioned in at least two groups of a plurality of transducers (305'-305") arranged in a spaced apart pattern on the external surface of the structures, the transducers individually transmit ultrasound signal into the pipe wall 204, in that each ultrasound signal propagates within the pipe wall 204 from the transmitting transducer and is received at one or several receiving transducers, and the received ultrasound signal is converted to an electrical signal by the receiving transducers and recorded by the transceiver (20). Measurements are performed by using a further plurality of transducers (406, 506) that are placed apart from the two groups of a plurality of transducers (305'-305"). There is also disclosed a method for guided-wave tomographic measurement or monitoring of wall thicknesses in the walls of pipes and similar structures producing a set of measurement data by using the apparatus.

9 Claims, 3 Drawing Sheets

(56) References Cited

OTHER PUBLICATIONS

Huthwaite, Peter, Alicia A. Zwiebel, and Francesco Simonetti. "A new regularization technique for limited-view sound-speed imaging." Ultrasonics, Ferroelectrics, and Frequency Control, IEEE Transactions on 60.3 (2013): 603-613.

Huthwaite, Peter, and Francesco Simonetti. "High-resolution guided wave tomography." Wave Motion 50.5 (2013): 979-993.

Nagy, Peter B., Francesco Simonetti, and Geir Instanes. "Corrosion and erosion monitoring in plates and pipes using constant group velocity Lamb wave inspection." Ultrasonics 54.7 (2014): 1832-1841.

Search Report Norwegian PTO, dated Nov. 20, 2015.

Willey, C. L., et al. "Guided wave tomography of pipes with high-order helical modes." NDT & E International 65 (2014): 8-21.

Prior art

METHODS AND APPARATUS FOR MEASUREMENT OR MONITORING OF WALL THICKNESSES IN THE WALLS OF PIPES OR SIMILAR STRUCTURES

FIELD OF THE INVENTION

The present invention relates to a method and apparatus for measurement or monitoring of wall thicknesses in the walls of pipes and similar structures.

THE STATE OF ART

There are several ongoing initiatives for providing two-dimensional maps of wall thickness in a section of pipe, being straight, bent, or having other geometries such as, e.g., reducers for connecting pipes of different diameters. The most sophisticated and also promising method for such mapping of wall thickness is guided-wave tomography as disclosed by G. Instanes, P. Nagy, F. Simonetti and C. Willey, in "Measuring wall thickness loss for a structure". USA Patent Application 20140208852, 31 Jul. 2014.

A typical apparatus for guided-wave tomography of pipe wall thickness consists of a control and processing unit 10, a transceiver unit 20 for ultrasound signal generation and acquisition, two or more ultrasound transducers 205, and material for permanently or temporarily affixing the transducers to the exterior pipe wall 204 surface 201 as shown in the enclosed FIG. 1.

A number of ultrasound transducers 205 are placed on the external surface 201 of, e.g., a section of pipe 200. The transducers 205 are preferably positioned in at least two groups of a plurality transducers (205'-205") arranged in a space apart pattern on the external surface of the pipe. More preferably, the transducer positions used for measurement are distributed in two circumferential rings 205', 205", one to each axial side of the area being monitored for wall thickness change, see FIG. 3. This strategy for transducer placement is utilized in all current implementations of guided-wave tomography systems for wall thickness mapping or monitoring of pipe sections, being straight or bent. Reasons for this transducer placement are at least twofold: The configuration is practical in field applications, and the transducer positions form a geometry that is beneficial for numerical processing of the measurement results to produce a two-dimensional tomographic wall thickness map.

The process of generating a tomographic wall thickness map consists of two main steps; measurement and data processing. First, a multitude of measurements are made in a pitch-catch mode of operation, operating one transducer at a time to transmit an ultrasonic guided wave signal, letting the signal propagate in the pipe wall, and subsequently receiving the propagated signal at one or several transducers. Although a single signal is transmitted at the transmitting transducer, each receiving transducer detects a multitude of signal arrivals because there exist a multitude of signal propagation paths between any two given positions on a pipe or bend as shown in FIG. 2. This multitude of paths traverse different parts of the pipe wall and also form different angles to the pipe axis, and thus provide in sum a variety of viewing angles at each location on the pipe wall. This multitude of propagation angles provides basis for two-dimensional resolution in a wall thickness map, or image, formed by tomographic data processing. A complete set of measurement data contains results from a fine mesh of guided-wave propagation paths covering the examined area of pipe wall. The arrival time and phase of the measured signals encode information about the average wall thickness along each traversed path.

Second, the complete set of measurement data is processed numerically to generate a two-dimensional representation of the wall thickness throughout the examined area of pipe wall, the pipe being straight or bent. This generation of a wall thickness map, or image-like representation, based on measurement data from intersecting curves, is referred to as tomography.

SHORTCOMINGS OF THE PRESENT TECHNOLOGY

Two considerable shortcomings of the present art are mentioned in the following: Firstly, the walls of a bent pipe has double curvature, which leads to focusing and defocusing effects that do not occur on walls of straight pipes. With the generally adopted two-ring transducer placements, very few transducer-to-transducer signal propagation paths intersect the outer side, or extrados, of the bend. As a result, the present art achieves poor wall thickness accuracy and resolution for the extrados region of bent pipes. This region is of particular interest in important applications for the technology, for example erosion monitoring in pipelines for oil and gas production. This shortcoming significantly weakens the applicability of guided-wave tomography for monitoring and inspection of pipe bends.

Secondly, various types of liquid loading and coatings on the pipe wall surfaces affect the guided wave signals and limit the orders of helical modes that carry useful measurement data. This is because higher order helical modes correspond to longer signal propagation paths and thus greater exposure to signal attenuation than lower order helical modes, as disclosed by F. Simonetti, "Lamb wave propagation in elastic plates coated with viscoelastic materials," J. Acoust. Soc. Am., vol. 115, no. 5, pp. 2041-2053, 2004, see also FIG. 2 for illustration. A lack of measurement data from higher-order helical modes can have detrimental effect on the axial resolution of tomographic wall thickness maps and also in general reduces the volume of measurement data on which calculations of wall thickness changes are founded.

OBJECTS OF THE PRESENT INVENTION

A main object of the present invention is to provide a new method and apparatus for determining changes over time in wall thickness of pipes, being straight or bent.

A further purpose of the invention is to provide a new method and apparatus in order to avoid the abovementioned disadvantages in examining changes in wall thickness over time.

In particular the object of the invention is to increase the measurement accuracy and resolution for measuring or monitoring wall thickness in pipes, being straight or bent.

SUMMARY OF THE INVENTION

The invention is the placement of ultrasound transducers within the area of pipe wall being examined, on locations that enhance the mesh of obtainable signal propagation paths, in terms of 1) high and homogeneous density of paths throughout the examined area and 2) variety of sound propagation angles (directions), necessary to achieve a sufficient measurement accuracy and two-dimensional resolution everywhere in the obtainable wall thickness map.

The method for guided-wave tomographic measurement or monitoring of wall thicknesses of the walls of pipes and similar structures is characterized in that use is made of transducers preferably positioned in at least two groups of a plurality of transducers arranged in a spaced apart pattern on the external surface of the pipe (or structure). The transducers individually transmit an ultrasound signal into the pipe wall and that ultrasound signal propagates within the pipe wall from the transmitting transducer and is received at one or several receiving transducers. The received ultrasound signal is converted to an electrical signal by the receiving transducer and recorded by the transceiver. In addition, measurements are performed by using a further plurality of transducers that are placed apart from the two groups of a plurality of transducers.

The apparatus for guided-wave tomographic measurement or monitoring of wall thicknesses in the walls of pipes and similar structures is characterized in that transducers are preferably positioned in at least two groups of a plurality of transducers arranged in a spaced apart pattern on the external surface of the pipe along with a transceiver unit for ultrasound signal generation and acquisition. In addition, a further plurality of transducers are placed within the area being examined and apart from two groups of a plurality of transducers.

The two aforementioned shortcomings of the present art are overcome by adding transducer positions elsewhere than within the two rings illustrated in FIG. 3.

A number of transducers 406 may for example be placed along the extrados (the outer side) of a pipe bend, as illustrated in (FIG. 4), or along an axially oriented line of a straight pipe section as illustrated in (FIG. 5). Such positioning of transducers allow additional guided-wave propagation paths that eliminate both of the aforementioned shortcomings of the present art. On a straight pipe section the additional transducer positions provide signal paths that resemble those of higher-order helical modes but yield shorter signal propagation distance and thus reduced signal loss due to coatings or liquids in contact with pipe surfaces.

Apart from the mechanical change to the measurement system, the invention comprises a conceptual change in the modelling approach, wherein there is mutual influence between instrument set-up and modelling results. Instead of adopting a classical and static "limited view problem" with solutions known from fields like medicine and seismic data analysis, a more adaptive data analysis scheme is necessary to make full use of transducer positions that may be anywhere on or adjacent to the area being examined.

DESCRIPTION OF THE DRAWINGS

Embodiments of the present invention will now be described, by way of example only, with reference to the following drawings wherein.

DESCRIPTION OF EMBODIMENTS OF THE INVENTION

Figure 1:
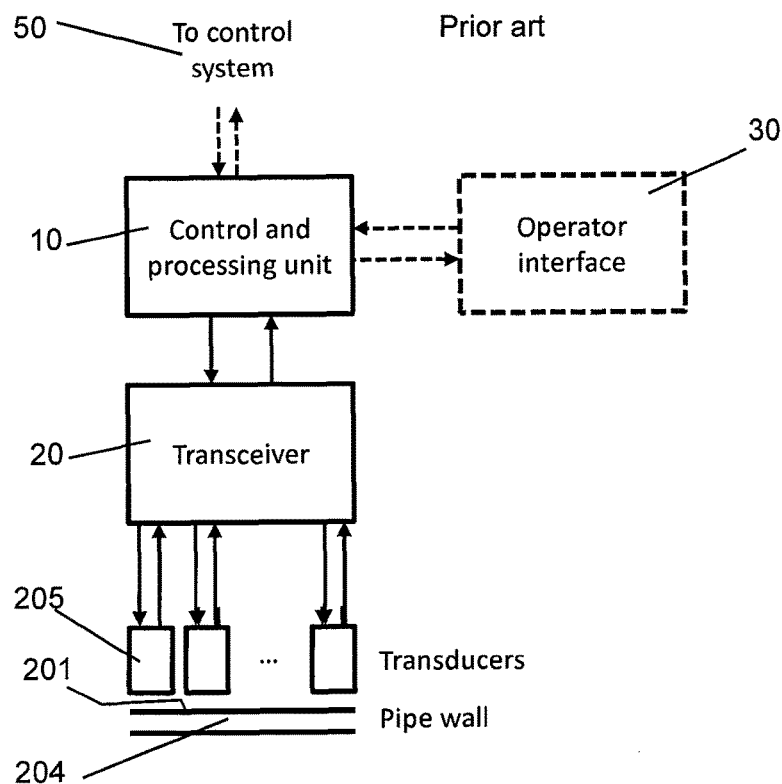
FIG. 1 shows a block diagram of a typical system for wall thickness monitoring by use of ultrasonic guided waves.

The invention is now explained more in detail by reference to FIG. 1.

FIG. 1 is an example block diagram of a system for monitoring wall thickness by means of ultrasonic guided waves. A control and processing unit 10 controls the measurements, which are performed at predetermined or automatically determined times. Typical intervals between measurements may be hours, days, or weeks depending on the expected rate of wall thickness loss and the application of the measurement results. For example, erosion due to sand and other particles in multiphase petroleum production flow, water cooling systems, or hydropower may in special cases lead to wall loss rates of several millimeters per hour. Internal and external corrosion of wall materials depend on chemical factors, temperature conditions, and flow properties, and may progress over months or years before any corrective action is required. Monitoring of the wall thicknesses may still be of paramount importance because loss of containment of many fluids can be catastrophic in for example petroleum production and processing and in nuclear power plants. In some cases the goal of monitoring or inspection may be to determine whether and when a section of pipe should be replaced. In other cases the results may be used to assess the efficiency of measures taken to reduce corrosion or erosion rates. The latter of these two examples may require significantly higher measurement accuracy than the former, as it may require quantification of minute changes in wall loss rates over time intervals as short as a few weeks.

The measurement results can optionally be made available to an operator through an operator interface 30, through which the measurement system can also be configured. The operator interface 30 may be local and/or remote. Measurement results can also optionally be communicated directly to the Control system 50 of a plant or to another electronic infrastructure.

A Transceiver 20 is controlled by the Control and processing unit 10 and connected to two or more electroacoustic Transducers 205. The transducers 205 are positioned on the exterior surface 201 of the wall 204 of a pipe 200 and are either permanently fixed, replaceable, or moveable along a trajectory on the Pipe wall surface 201. Each transducer 205 may be used for signal transmission from the Transceiver 20 into the pipe wall 204, signal reception from the pipe wall to the Transceiver, or both.

A measurement series can be said to comprise the following steps:

1. The Transceiver 20 generates an ultrasound signal and transmits it into the Pipe wall 204 by means of one Transducer 205.

2. The said ultrasound signal propagates within the Pipe wall 204 from the said transmitting Transducer 205 and is received at one or several receiving Transducers.

3. The said received ultrasound signal is converted to an electrical signal by the receiving Transducers and recorded by the Transceiver.

Steps 1-3 are repeated until ultrasound transmission has been carried out between all necessary pairs of positions for signal transmission and reception on the Pipe wall. The recorded signals are transferred to the Control and processing unit and then subjected to a numerical procedure for tomographic imaging. By comparison with results from earlier measurements, a two-dimensional map of wall thickness changes is produced.

Figure 2:
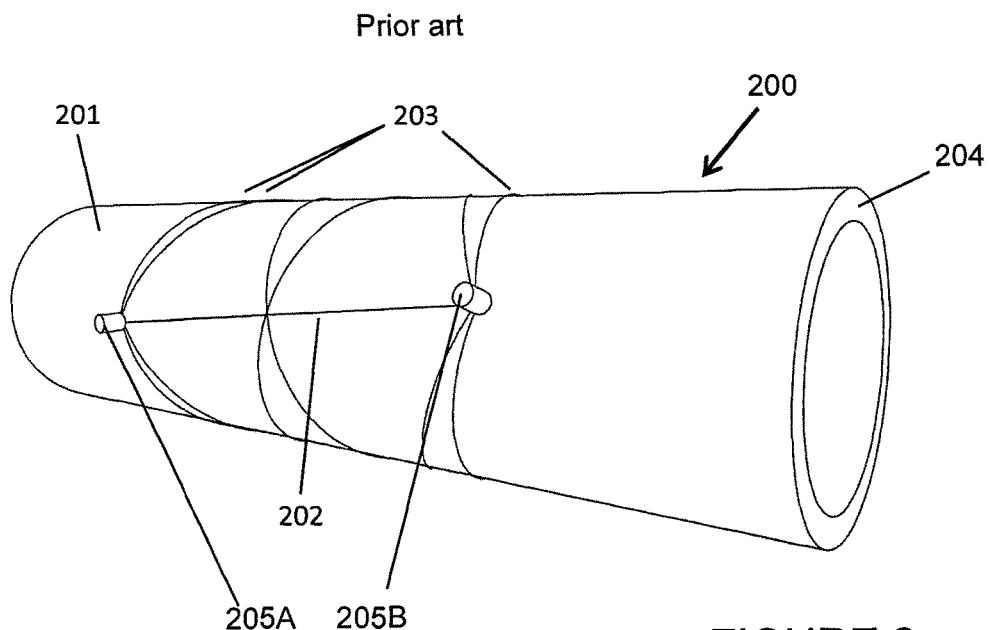
FIG. 2 shows direct and helical modes of guided wave propagation in a pipe wall.

Reference is now made to FIG. 2 illustrating direct and helical modes of guided wave propagation in a wall 204 of a pipe 200. The direct mode is due to sound propagation along the shortest path 202 between a pair of transmitting and receiving transducers 205A and 205B, respectively. In addition to the direct mode there may exist an infinite number of helical modes due to signal propagation paths 203 that go around the circumference of the pipe. There are two helical modes of each order, corresponding to signal travel in a positive (counterclockwise) or negative (clockwise) angular direction around the pipe circumference. The order may be 0, 1, 2, or higher, relating to the number of rotations around the pipe, order 0 referring to the direct path. The illustration in FIG. 2 includes the five signal propagation paths 202, 203 corresponding to the zeroth, first, and second order helical modes. The use of helical modes adds axial resolution to two-dimensional maps of wall thickness changes and also generally contribute to the volume of measurement data used for tomographic imaging.

Figure 3:
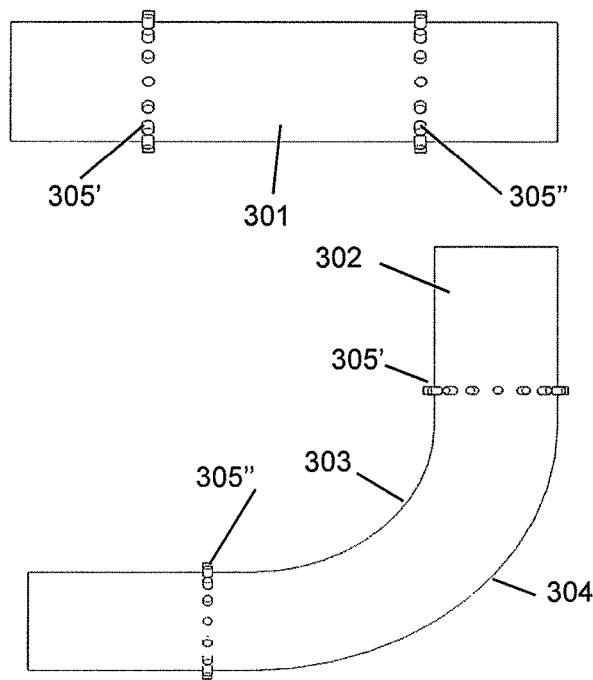
FIG. 3 shows transducers mounted on straight and bent pipes according to the present art.

FIG. 3 illustrates positions for receiving and transmitting ultrasound transducers 305 placed on a section of straight pipe 301 and a pipe bend 302 according to the present state of the art of tomographic wall thickness measurement and monitoring. The placement of transducers in rings around the circumference of the pipe is practical for installation and measurement using fixed or moveable transducers, and the obtainable measurement results conform to conventional tomography problems known from e.g. seismology as a "cross-borehole", or "limited view", tomography problem as disclosed by K. R. Leonard and M. K. Hinders, "Guided wave helical ultrasonic tomography of pipes," J. Acoust. Soc. Am., vol. 114, p. 767, 2003. The inventors are not aware of any other choice of transducer positions used according to the present state of the art—see also the following:

A. Volker and T. van Zoon, "Guided Wave Travel Time Tomography for Bends," in 18th World Conference on Non destructive Testing, 16-20 Apr. 2012, Durban, South Africa, 2012.

B. C. L. Willey, F. Simonetti, P. B. Nagy and G. Instanes, "Guided wave tomography of pipes with high-order helical modes," NDT & E International, vol. 65, pp. 8-21, 2014.

C. T. van Zon and A. Volker, "Guided wave travel time tomography for quantitative wall thickness mapping," in 11th European Conference on Non-Destructive Testing (ECNDT 2014), October 6-10, Prague, Czech Republic, 2014.

D. A. J. Brath, F. Simonetti, P. B. Nagy and G. Instanes, "Acoustic formulation of elastic guided wave propagation and scattering in curved tubular structures," IEEE Trans. Ultrason. Ferroelect. Freq. Control, vol. 61, pp. 815-829, 2014.

However, studies made by the inventors (e.g., in reference D) indicate that positioning of transducers 305 in rings on either side of pipe bends 302 leads to very few guided-wave signal paths that cover the extrados region 304 of such bends. Simulations and experiments confirm that this transducer placement leads to wall thickness measurements with increased sensitivity to wall thickness loss in the intrados region 303 of such bends and reduced sensitivity towards wall thickness loss in the extrados region 304.

Figure 4:
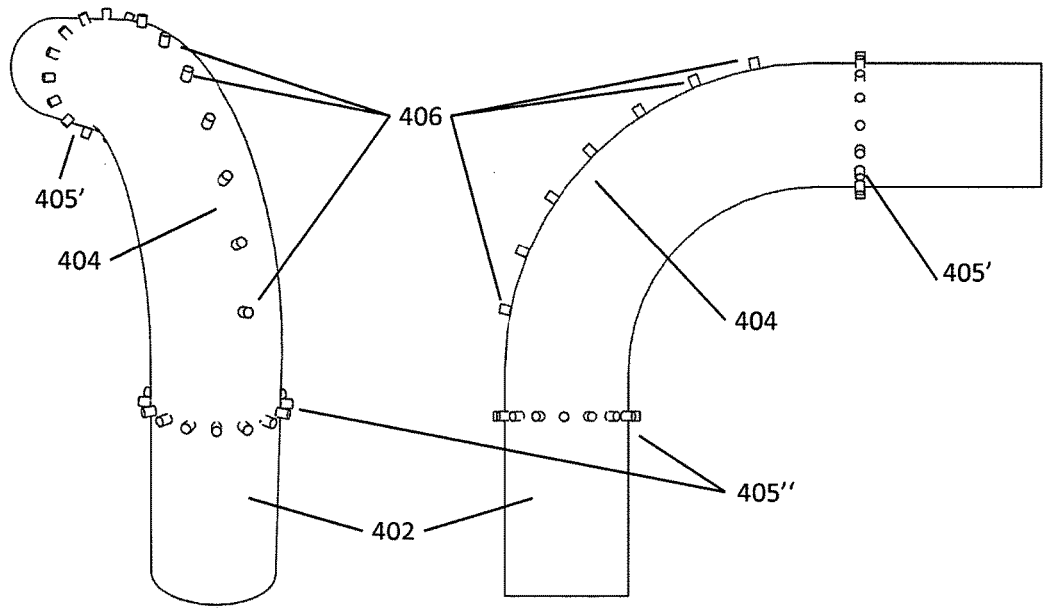
FIG. 4 illustrates the present invention in the case of a bent pipe, which is the adding of transducers 406 between the rings of transducers.

FIG. 4 illustrates an example of a realization of the present invention, which is the adding of transducers 406 between the rings of transducers 405',405". In this example transducers are positioned along the extrados 404 of a bend 402. The invention includes arbitrary transducer placements that are typically predicted by simulations to yield desired density and direction of signal propagation paths within regions to be examined on the pipe wall 402. The examined section of pipe may be straight or bent, and may have variable wall thickness and diameter such as, e.g., a reducer. The example of FIG. 4 shows the pipe bend connecting the two straight pipe sections, forming in total a bend of 90 degrees, in that the that each ring of transducers 405' and 405" are placed in the straight sections adjacent the start of the bend or curved pipe section to control and examine for any erosion of the pipe thickness of bend over time. In addition, further lines or rows of transducers 406 may be placed along the extrados section of the bend between the two rings 405',405" of transducers, and possibly also in positioned in the intrados region of the pipe. The extra transducers may be arranged mutually in parallel between the two ring structures 405'-405". Either forming straight lines or waveforms, or they are formed in random patterns along the surface of the pipe between the to transducer structures 405'-405".

Figure 5:
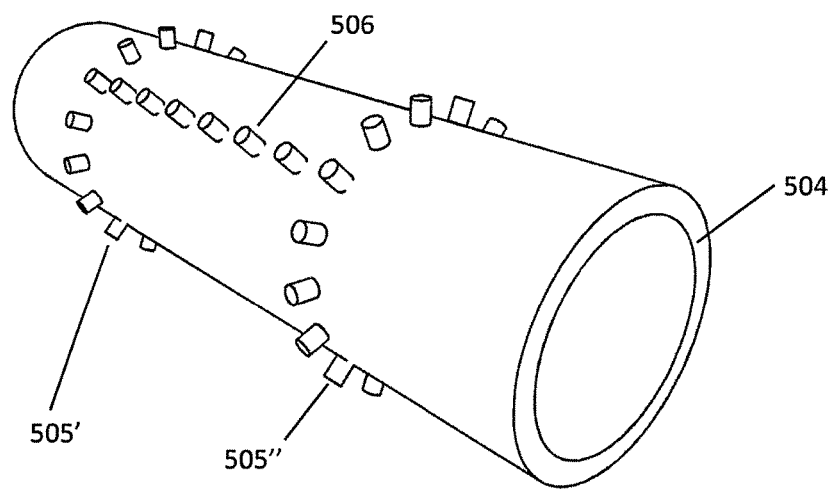
FIG. 5 illustrates the present invention in the case of a straight pipe, which is the adding of transducers 506 between the rings of transducers

FIG. 5 illustrates a second example of a realization of the invention, which is the adding of transducers 506 between the rings of transducers 505',505" on a section of straight pipe 504. The added transducers 506 provide signal paths that resemble those of higher-order helical modes but yield shorter signal propagation distance and thus reduced signal loss due to coatings or liquids in contact with the surfaces of the pipe 504. For this version also further lines or rows of transducers 506 may be placed on and along the pipe surface between the two rings 405',405" of transducers, in that they may be arranged mutually in parallel along the pipe surface.

What is claimed is:

1. Method for guided-wave tomographic measurement or monitoring of wall thicknesses of the walls of pipes and similar structures, wherein characterized in that use is made of transducers preferably positioned in at least two groups of a plurality of transducers arranged in a spaced apart pattern on the external surface of the said structures, said transducers individually transmit ultrasound signal into the pipe wall, in that said ultrasound signal propagate within the pipe wall from the said transmitting transducer and is received at one or several receiving transducers, and said received ultrasound signal is converted to an electrical signal by the receiving transducers and recorded by the a transceiver (20), and further characterized in that measurements are performed by using a further plurality of transducers that are placed apart from the said two groups of a plurality of transducers and in that said further transducers are arranged in at least one line or curve parallel to the length axis of the examined structure between the two groups of transducers.

2. Method according to claim 1 characterized in that where the examined structure is a straight or bent pipe, the measurements are performed with the said two transducer groups arranged in two rings around the pipe circumference.

3. Method according to claim 1 characterized in that where the examined structure is a bent pipe the measurements are performed with the further transducers placed on the extrados of the pipe bend to provide transducer-to-transducer signal propagation paths that intersect the extrados (outer side) of the pipe wall of the bend.

4. Apparatus for guided-wave tomographic measurement or monitoring of wall thicknesses in the walls of pipes and similar structures comprising transducers positioned in at least two groups of a plurality of transducers are arranged in a spaced apart pattern on the external surface of the pipe, and a transceiver unit for ultrasound signal generation and acquisition, and characterized in that a further plurality of transducers are placed on the pipe surface in one or more rows or lines between said two groups of a plurality of transducers.

5. Apparatus according to claim 4 characterized in that where the examined structure is a straight or bent pipe, the groups of transducers are arranged in two rings around the pipe circumference.

6. Apparatus according to claim 4 characterized in that said further transducers are placed in a pattern on the pipe wall between said groups of transducers.

7. Apparatus according to claim 4 characterized in that where the examined structure is a bent pipe said further transducers are placed on the extrados of the pipe bend to provide transducer-to-transducer signal propagation paths to intersect the extrados (outer side) of the pipe wall of the bend.

8. Method for guided-wave tomographic measurement or monitoring of wall thicknesses in the walls of pipes and similar structures producing a set of measurement data by using the apparatus according to claim 4 characterized by the following steps:

1. the transceiver unit generates an ultrasound signal and transmits it into the pipe wall by means of one transducer,
2. the said ultrasound signal propagates within the pipe wall from the said transmitting transducer and is received at one or several receiving transducers,
3. the said received ultrasound signal is converted to an electrical signal by the receiving transducers and recorded by the transceiver, and steps 1-3 are repeated until ultrasound transmission has been carried out between pairs of positions for signal transmission and reception on the pipe wall.

9. Method according to claim 8 characterized in that the recorded signals are subjected to a numerical procedure for tomographic imaging, and, by comparison with earlier measurement results, a two-dimensional map of wall thickness changes is produced.

* * * * *